US012609502B2

(12) United States Patent
Kokovidis et al.

(10) Patent No.: US 12,609,502 B2
(45) Date of Patent: Apr. 21, 2026

(54) MODULAR CONNECTOR SYSTEM AND A MODULAR CONNECTOR HAVING TWO OR MORE DETACHABLY SECURED HOUSINGS

(71) Applicant: Drägerwerk AG & Co. KGaA, Lübeck (DE)

(72) Inventors: Georgios Kokovidis, Waltham, MA (US); Rajesh S. Rane, Andover, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 850 days.

(21) Appl. No.: 17/790,343

(22) PCT Filed: Dec. 22, 2020

(86) PCT No.: PCT/IB2020/062363
§ 371 (c)(1),
(2) Date: Jun. 30, 2022

(87) PCT Pub. No.: WO2021/137110
PCT Pub. Date: Jul. 8, 2021

(65) Prior Publication Data
US 2023/0108418 A1     Apr. 6, 2023

Related U.S. Application Data

(60) Provisional application No. 62/954,871, filed on Dec. 30, 2019.

(51) Int. Cl.
*H01R 27/02*     (2006.01)
*A61B 5/145*     (2006.01)
(Continued)

(52) U.S. Cl.
CPC ......... *H01R 27/02* (2013.01); *A61B 5/14542* (2013.01); *A61B 5/303* (2021.01);
(Continued)

(58) Field of Classification Search
CPC .... H01R 27/02; H01R 13/6273; H01R 31/06; H01R 2201/12; H01R 13/514;
(Continued)

(56) References Cited

U.S. PATENT DOCUMENTS

| | | | |
|---|---|---|---|
| 5,192,226 A | 3/1993 | Wang | |
| 5,582,180 A | * 12/1996 | Manset ................. | A61B 5/308 |
| | | | 600/382 |
| 2019/0175047 A1 | 6/2019 | Verbakel et al. | |

FOREIGN PATENT DOCUMENTS

| | | |
|---|---|---|
| EP | 3527129 A1 | 8/2019 |
| WO | 2015094248 A1 | 6/2015 |

OTHER PUBLICATIONS

European Patent Office, The International Search Report and The Written Opinion of the International Searching Authority, Apr. 8, 2021, for International Application No. PCT/IB2020/062363.

* cited by examiner

*Primary Examiner* — Briggitte R. Hammond
(74) *Attorney, Agent, or Firm* — Nolte Lackenbach Siegel

(57)     ABSTRACT

A connector may include a first housing configured to detachably secure a first input cable of a first sensor configured to generate a first signal, and a second housing configured to detachably secure a second input cable of a second sensor configured to generate a second signal. The second housing may be configured to transmit the second signal from the second input cable to the first housing. The first housing may be configured to transmit at least one of the first signal and the second signal to an output cable. A coupling of the first housing may be configured to mate with a coupling of the second housing such that the first housing and the second housing are configured to be detachably secured to each other. The coupling may be mechanical, (Continued)

electro-mechanical, or magnetic. Either sensor may be an electrocardiogram sensor or a pulse oximetry sensor.

21 Claims, 5 Drawing Sheets

(51) Int. Cl.

| | |
|---|---|
| *A61B 5/30* | (2021.01) |
| *A61B 5/304* | (2021.01) |
| *A61B 5/308* | (2021.01) |
| *A61B 5/33* | (2021.01) |
| *A61B 5/339* | (2021.01) |
| *H01R 13/627* | (2006.01) |
| *H01R 31/06* | (2006.01) |

(52) U.S. Cl.
CPC .............. *A61B 5/304* (2021.01); *A61B 5/308* (2021.01); *A61B 5/33* (2021.01); *A61B 5/339* (2021.01); *H01R 13/6273* (2013.01); *H01R 31/06* (2013.01); *A61B 2560/0214* (2013.01); *A61B 2560/045* (2013.01); *A61B 2562/222* (2013.01); *A61B 2562/227* (2013.01); *H01R 2201/12* (2013.01)

(58) Field of Classification Search
CPC ......................... H01R 24/28; H01R 2107/00; A61B 5/14542; A61B 5/303; A61B 5/304; A61B 5/308; A61B 5/33; A61B 5/339; A61B 2560/0214; A61B 2560/045; A61B 2562/222; A61B 2562/227

See application file for complete search history.

MODULAR CONNECTOR SYSTEM AND A MODULAR CONNECTOR HAVING TWO OR MORE DETACHABLY SECURED HOUSINGS

CROSS-REFERENCE TO RELATED APPLICATIONS

This application is a national stage application of International Patent Application No. PCT/IB2020/062363 filed on Dec. 22, 2020, under 35 U.S.C. § 371, which claims the benefit of U.S. Prov. Pat. App. Ser. No. 62/954,871, filed on Dec. 30, 2019. Priority to and the benefit of U.S. Prov. Pat. App. Ser. No. 62/954,871 and International Patent Application No. PCT/IB2020/062363 is hereby claimed for all purposes, including the right of priority.

FIELD

The present disclosure generally relates to a system and a connector that can quickly and/or compactly expand the numbers and types of input ports for cables, and therefore the numbers and types of devices that can be supported. The cables may be configured to physically and electrically connect to one or more devices.

BACKGROUND

Conventional connectors generally are not modular or scalable and accordingly the number of devices that can be supported is fixed. Commonly, either a lower capacity conventional connector with a lower number of input ports must be used or a higher capacity conventional connector with a higher number of input ports must be used.

As an example, electrocardiogram (ECG) monitoring includes measuring biopotential signals indicative of an electrical activity associated with each cardiac activity (heartbeat) of a patient, by placing electrode sets on the skin of the patient. Commonly used ECG configurations include 3-lead, 5-lead, 6-lead and 12-lead configurations. In a 12-lead ECG configuration, for example, ten electrodes are placed on predetermined locations of the skin of the patient body. The overall magnitude of the heart's electrical potential is then measured from twelve different angles ("leads") and is recorded over a period of time (e.g., 10 seconds). In this way, the overall magnitude and direction of the heart's electrical activity is captured throughout the heartbeat. Depending on the need of the patient (e.g., medical condition of the patient, location of the patient, ECG monitoring device the patient is connected to, and/or medical procedure the patient is applied to), different lead configurations may be used. Additionally, 16-lead ECG configuration goes further beyond the 12-lead configuration, providing extended interpretations for adult chest pain by adding optional right chest and back electrodes, and detailed interpretation of rhythm and morphology for a wide variety of patient populations.

However, to switch between different lead configurations, a user must first fully disconnect one configuration and then replace it with another desired monitoring configuration. That is, the user is required to remove connectors as well as input/output cables for one ECG configuration, and subsequently place a different set of connectors and input/output cables for another ECG configuration, which adversely affect continuous monitoring required in the patient care.

SUMMARY

One or more embodiments provide:

(1) A connector including: a first housing configured to detachably secure a first input cable of a first physiological sensor configured to generate a first signal corresponding to a first physiological parameter of a patient; and a second housing configured to detachably secure a second input cable of a second physiological sensor configured to generate a second signal corresponding to a second physiological parameter of the patient, wherein: the second housing is configured to transmit the second signal from the second input cable to the first housing; the first housing is configured to transmit at least one of the first signal and the second signal to an output cable; and a coupling of the first housing is configured to mate with a coupling of the second housing such that the first housing and the second housing are configured to be detachably secured to each other.

(2) A system including: a connector including a first housing configured to detachably secure a first input cable of a first physiological sensor configured to generate a first signal corresponding to a first physiological parameter of a patient, and a second housing configured to detachably secure a second input cable of a second physiological sensor configured to generate a second signal corresponding to a second physiological parameter of the patient; and an output cable configured to be detachably secured to the first housing, wherein: the second housing is configured to transmit the second signal from the second input cable to the first housing; the first housing is configured to transmit at least one of the first signal and the second signal to the output cable; and a coupling of the first housing is configured to mate with a coupling of the second housing such that the first housing and the second housing are configured to be detachably secured to each other.

(3) A system including: a monitor; a connector including a first housing configured to detachably secure a first input cable of a first physiological sensor configured to generate a first signal corresponding to a first physiological parameter of a patient, and a second housing configured to detachably secure a second input cable of a second physiological sensor configured to generate a second signal corresponding to a second physiological parameter of the patient; and an output cable configured to be detachably secured to the first housing and the monitor, wherein: the second housing is configured to transmit the second signal from the second input cable to the first housing; the first housing is configured to transmit at least one of the first signal and the second signal to the output cable; and a coupling of the first housing is configured to mate with a coupling of the second housing such that the first housing and the second housing are configured to be detachably secured to each other.

(4) The connector or system of any of the above (1) to (3), further including: a third housing configured to detachably secure a third input cable of a third physiological sensor configured to generate a third signal corresponding to a third physiological parameter of the patient, wherein the third housing is configured to be detachably secured to at least one of the first housing and the second housing.

(5) The connector or system of any of the above (1) to (4), wherein: the third housing is configured to transmit the third signal from the third input cable to at least one of the first housing and the second housing.

(6) The connector or system of any of the above (1) to (5), wherein: the first housing includes at least one input port; and the second housing includes at least one input port.

(7) The connector or system of any of the above (1) to (6), wherein at least one of the coupling of the first housing and the coupling of the second housing is a mechanical coupling.

(8) The connector or system of any of the above (1) to (7), wherein the coupling of the first housing and the coupling of the second housing are configured to snap together.

(9) The connector or system of any of the above (1) to (8), wherein one of the coupling of the first housing and the coupling of the second housing includes a projection and the other of the coupling of the first housing and the coupling of the second housing includes a slot configured to receive the projection.

(10) The connector or system of any of the above (1) to (9), wherein at least one of the coupling of the first housing and the coupling of the second housing is an electro-mechanical coupling.

(11) The connector or system of any of the above (1) to (10), wherein at least one of the coupling of the first housing and the coupling of the second housing is a magnetic coupling.

(12) The connector or system of any of the above (1) to (11), wherein the second housing does not include an output port and therefore is configured to provide only an input port for the second input cable.

(13) The connector or system of any of the above (1) to (12), wherein the second housing can only be powered and communicate when secured or otherwise connected to the first housing.

(14) The connector or system of any of the above (1) to (13), wherein the second housing is detachably secured only to the first housing.

(15) The connector or system of any of the above (1) to (14), wherein the first housing and the second housing are physically connected only by the coupling of the first housing and the coupling of the second housing.

(16) The connector or system of any of the above (1) to (15), wherein the coupling of the first housing and the coupling of the second housing are configured to be detachably secured to each other such that one side of the second housing overlaps one side of the first housing.

(17) The connector or system of any of the above (1) to (16), wherein the coupling of the first housing and the coupling of the second housing are configured to be detachably secured to each other such that the at least one input port of the first housing and the at least one input port of the second housing are positioned on a single side of the connector.

(18) The connector or system of any of the above (1) to (17), wherein at least one of the first physiological sensor and the second physiological sensor is an electrocardiogram sensor.

(19) The connector or system of any of the above (1) to (18), wherein at least one of the first physiological sensor and the second physiological sensor is a pulse oximetry sensor.

BRIEF DESCRIPTION OF THE DRAWINGS

The following detailed description references the drawings, wherein.

DETAILED DESCRIPTION

Figure 1:
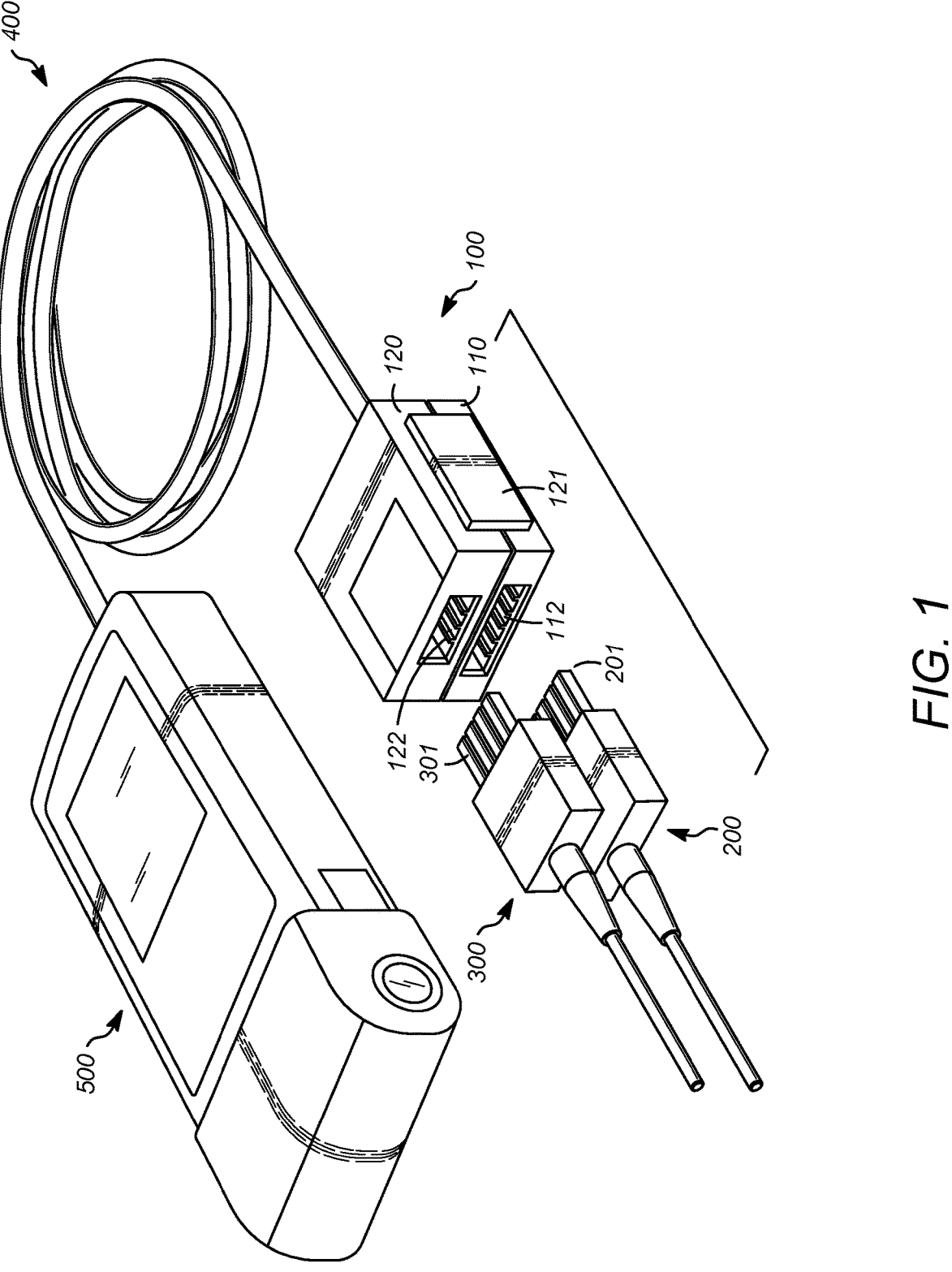
FIG. 1 is an overview of an example system including a first example implementation of a connector according to one or more embodiments.

The following description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

The terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

Features from different embodiments may be combined to form further embodiments, unless specifically noted otherwise. Variations or modifications described with respect to one of the embodiments may also be applicable to other embodiments. In some instances, well-known structures and devices are shown in block diagram form rather than in detail in order to avoid obscuring the embodiments.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It is to be understood that the singular forms "a", "an", and "the", include plural referents unless the context clearly dictates otherwise. Thus, for example, reference to "a connector" or "a cable" includes reference to one or more of such connectors or cables.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", etc., may modify various elements. However, such elements are not limited by the above expressions nor do the above expressions imply that there are just the requisite number of elements present. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

The subject matter described herein is directed to a system and a connector directed to a medical device (e.g., a patient physiological monitor and a physiological sensor), and a module. A patient monitor is used by healthcare facilities to monitor and display information about a patient, such as vital signs, status of connected devices (e.g., physiological sensors), etc. A patient monitor can be a portable device that travels with the patient in order to provide continuous monitoring during care.

A physiological sensor and/or medical device can be, for example, an electrocardiogram (ECG) electrode, an oxygen saturation ($SpO_2$) sensor, a blood pressure cuff, an apnea detection sensor, a respirator, etc., and can measure a physiological parameter of a patient (e.g., gas measurement, end-tidal carbon dioxide (etCO2), near infrared spectroscopy (NIR), patient gas, thermoregulation, blood pressure, heart related measurement, pulse oximetry, respiration, neonatal measurement, ventilation, anesthesia information, incubation information, etc.).

A module can provide one or more different functions used in delivering healthcare to a patient. A module can acquire patient data including the monitored parameters allocated to a given patient from a network and collate the information for storage in a database. A module can be any of a patient monitoring module for acquiring and processing data generated by at least one physiological sensor, a patient treatment module for delivering treatment to the patient (e.g., monitoring fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, an output board, a dock module, an adapter module, a passive treatment module, an active treatment module, etc. Use of such systems and apparatuses can, for example, occur in a medical environment such as the scene of a medical event, an ambulance, a hospital or a doctors office.

Conventional connectors impede standard clinical workflow because the number of inputs ports is fixed and cannot be increased. Consequently, if enhanced functionality is desired, a lower capacity conventional connector must be replaced with a higher capacity conventional connector and any associated cables must be disconnected and reconnected. The capacity of a conventional connector itself cannot be expanded. In hospital settings where high acuity care is necessary, unscalable connection arrangements are particularly time-consuming and burdensome.

Furthermore, higher capacity conventional connectors are not as compact and require more space than lower capacity conventional connectors. In some instances, a device such as a monitor itself may include a higher capacity conventional connector permanently built into a front end thereof. However, this is disadvantageous because it requires the design of such devices to be more complex and also requires an increase in the size of such devices.

In some instances, another monitoring device for monitoring a different physiological parameter may be additionally needed during the monitoring or therapeutic process, and the lower or higher capacity conventional connector must be replaced by more connectors and input/output cables to accommodate different devices. Such configurations cannot fulfill the need of flexible and continuous monitoring of different types of physiological parameters.

Therefore, a need exists to provide a connector that can expand the number of input ports for cables, and/or remove the burden of having higher capacity connectors within devices themselves.

The object of the present disclosure is to provide a system and a connector that can solve one or more of the aforementioned problems or similar problems by being able to quickly and/or compactly expand the number of input ports for cables, and therefore the number of devices that can be supported.

The connector of the present disclosure can be standardized and can consolidate a plurality of inputs for cables. The connector of the present disclosure can be tailored to meet the specific connection needs of a user. The connector of the present disclosure therefore optimizes workflow through well-structured workplace design by reducing cable routing time. Cable and/or connector disconnection and reconnection can cause a great deal of frustration, lost time, and patient discomfort. Managing conventional connectors is a tedious, time-consuming distraction that takes focus away from patient care. As connectors and/or cables are attached, they must be properly connected and routed. The connector of the present disclosure minimizes the time to switch from a lower capacity connection arrangement to a higher capacity connection arrangement or vice versa, thereby enabling caregivers to spend more time with patients and less time sorting out cables. The connector of the present disclosure is space efficient while also providing a higher capacity connection arrangement. In particular, the connector of the present disclosure is more compact than higher capacity conventional connectors. In addition, the connector of the present disclosure allows the design of associated devices to be simplified and the size of the associated devices to be reduced. As an example, the connector of the present disclosure itself can provide a connection interface for ECG monitoring instead of an associated device such as a monitor having to provide such connection interface.

Figures 2A, 2B:
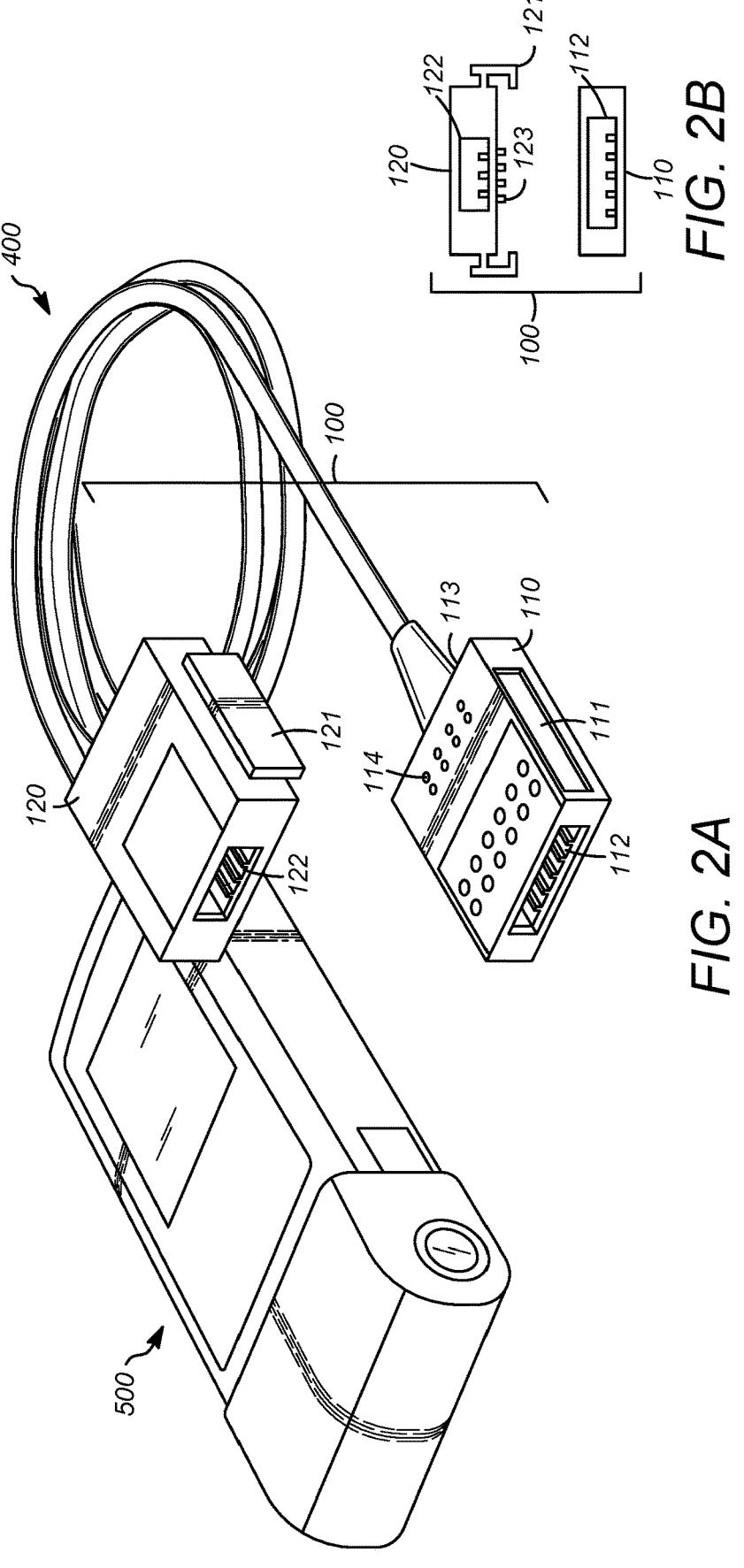
FIG. 2A is a perspective view illustrating the example system including the first example implementation of the connector, an output cable, and a monitor according to one or more embodiments.
FIG. 2B is a front view of the first example implementation of the connector 100 including a first and a second housing according to one or more embodiments.

FIG. 1 is a perspective view illustrating an example system including a first example implementation of a connector 100, a first input cable 200, a second input cable 300, an output cable 400, and a monitor 500. In the embodiment shown in FIG. 1, the connector 100 includes a first housing 110 and a second housing 120. As illustrated in FIGS. 2A and 2B and described in further detail below, the connector 100 is a modular design that enables one or more housings to be connected to be added to the first housing 110. The additional housing(s) (e.g., second housing 120) enable(s) the first housing 110 to receive data from the additional housing(s) and transmit the data to a monitor 500.

The monitor 500 is a multifunction monitoring device that includes at least one processor that is configured to process one or more types of physiological sensor data (e.g., measurement signals) measured at a patient. As described in reference to FIG. 5, the monitor 500 not only processes the physiological sensor data but includes a display that displays the various types of physiological sensor data thereon.

One advantage of the current implementation is that the additional housing(s) may be added, but only one output cable 400 is used. This reduces the amount of cables and input connections required by the monitor 500. Likewise, it reduces tangled clutter and hazards between the connector and the monitor that frequently occur with traditional cables and reduces visual overload for medical professionals and patients. It also avoids a plurality of connectors from being directly positioned into input ports at a front end of the monitor which requires more complex design and size increase in the monitor.

Additionally, the modular design of the illustrated example, enables a medical professional to quickly add additional leads of a second cable 300 by connecting the second cable 300 to the second (or third) housing 120, which is connected and is communicatively coupled to the first housing 110. Put another way, the modular design prevents a medical professional from having to disconnect a first housing and then reattach and reconnect a separate dedicated cable for a 12-lead ECG. The opposite is also true. That is, a medical professional can switch from a 12-lead to 6-lead configuration without needing to disconnect and reconnect cables from the first housing 110. Instead, an ECG lead configuration may be changed by adding or removing a cable from housing 120 or any other additional housing, or by disconnecting housing 120 or any other additional housing from housing 110. It is understood that the first housing 110 and its input cable 200 remain connected to monitor 500, for example, via output cable 400.

It is noted that each cable 200, 300, etc., may be a "smart" cable in that it comprises a processor (e.g., an EEPROM) that is embedded therein and can operate to some extent interactively and autonomously with another device. The processor may be an EEPROM, a central processing units (CPU), a digital signal processor (DSPs), a general purpose microprocessor, an application specific integrated circuit (ASIC), a field programmable logic array (FPGA), or other equivalent integrated or discrete logic circuitry. For example, the processor may be embedded in a connector of the ECG lead set (i.e., a cable). The processor is configured to store data relevant to the ECG lead set and the monitor 500 is capable of carrying out both read and write operations with respect to the stored data (e.g., EEPROM data).

For example, the number of leads of various types of ECG lead sets can vary. For example, existing ECG lead sets have anywhere between 3-wires to 10-wires. However, any number of leads is possible. The monitor 500 requires information regarding how many leads are present in the ECG lead set to allow for proper processing and display of ECG data. The EEPROM of each cable 200, 300 may be configured to send this information autonomously after it autonomously detects a connection made to the monitor 500. This communication exchange between an EEPROM of each cable 200, 300 occurs through the first and second housings 110 and 120. With respect to the second housing, the EEPROM data from cable 300 is provided to the monitor 500 through the first housing 110 via the appropriate first and second connection interfaces 114, 123 and the routing circuitry providing in the first housing that connects the first connection interface 114 to the output cable 400.

As such, two or more input cables 200, 300 can be connected to the connector via housings 110, 120, ..., with the output from housing 110 transmitted to output cable 400 including all electrical signals provided by the connected housings 110, 120. The monitor 500 is configured to receive the signals and process them according to received EEPROM data, for example. In particular, the monitor 500 is configured to receive EEPROM data from each input cables 200, 300 and determine a configuration based on cable type (e.g., ECG, spO2, etc.) and number of leads.

If multiple ECG cables are connected the monitor 500 is further configured to automatically configure itself, via its one or more processors, to use the most enhanced ECG lead set configuration from the combination of lead sets based on EEPROM data received from each of the input cables 200, 300. In other words, the monitor 500 determines the total number of ECG leads to which it is connected via housings 110, 120, etc., (i.e., the total number of ECG leads from the input cables) and optimizes the ECG configuration according to the total number of connected ECG leads. For example, if ten ECG leads are connected, the monitor 500 uses a 12-lead ECG configuration. If fourteen ECG leads are connected, a 16-lead ECG configuration is used.

On the other hand, if the second input cable 300 or any additional ECG input cable is disconnected, the monitor 500 automatically reconfigures its ECG lead configuration to account for the cable disconnect. Thus, the monitor 500 may automatically reduce its ECG lead configuration from, for example, a 12-lead ECG configuration to a 6-lead ECG configuration in response to a disconnect of the second input cable 300. It does this in response to no longer detecting the electrical signals corresponding to the second input cable 300.

If the input cables 200, 300 are different types that provide different types of sensor data (e.g., ECG, spO2, etc.), the monitor 500 is configured to detect both types of sensor data for appropriate processing.

Yet another advantage of the modular housings (e.g., 110 and 120) is that if more cables are required (e.g., 16 leads or more), the modular design of the housings enable additional housings to be secured to the first housing 110. A single cable from the first housing 110 is able to transfer the data. While the illustrated example shows a cable 400 connecting the first housing 110 to the monitor 500, there could be a wireless interface between the first housing 110 and the monitor 500. Thus, cable 400 may be representative of a wired or wireless communication channel that transmits data received from the first housing 110 to the monitor 500.

The first housing 110 may be configured to detachably secure the first input cable 200 by receiving at least one pin 201 of the first input cable 200 in at least one input port 112 of the first housing 110. The first input cable 200 may be connected to one portion of a first physiological sensor (e.g., one or more electrodes of an ECG sensor or a pulse oximeter probe applied to a patient's finger, toe, or earlobe) configured to generate a first signal corresponding to a first physiological parameter of a patient.

The second housing 120 may be configured to detachably secure the second input cable 300 by receiving at least one pin 301 of the second input cable 300 in at least one input port 122 of the second housing 120. The second input cable 300 may be connected to one portion of a second physiological sensor (e.g., one or more electrodes of an ECG sensor or a pulse oximeter probe applied to a patient's finger, toe or earlobe) configured to generate a second signal corresponding to a second physiological parameter of the patient. The second housing 120 may be configured to transmit the second signal from the second input cable 300 to the first housing 110, e.g., via an electrical coupling. Either of the first signal and the second signal can be, for example, a digital signal or an analog signal.

The first housing 110 may include at least one output port 113 configured to receive a first end of the output cable 400. The monitor 500 may be configured to receive a second end of the output cable 400. The first housing 110 may be configured to transmit at least one of the first signal and the second signal to the output cable 400 and/or the monitor 500.

A coupling 111 of the first housing 110 may be configured to mate with a coupling 121 of the second housing 120 such that the first housing 110 and the second housing 120 may be configured to be mechanically, yet detachably, secured to each other. In the embodiment shown in FIG. 1, the second housing 120 may be detachably secured only to the first housing 110 and may not be directly secured to any other element of the system. In the embodiment shown in FIG. 1, the first housing 110 and the second housing 120 may be physically connected only by the coupling 111 (which is illustrated in FIGS. 2A and 2B and described in detail below) of the first housing 110 and the coupling 121 of the second housing 120. The coupling 111 of the first housing 110 and the coupling 121 of the second housing 120 may be configured to be detachably secured to each other such that one side of the second housing 120 overlaps one side of the first housing 110.

In the embodiment shown in FIG. 1, the one side of the first housing 110 may face and correspond to the one side of the second housing 120. For example, a length of the first housing 110 may correspond to a length of the second housing 120 and/or a width of the first housing 110 may correspond to a width of the second housing 120. Furthermore, the coupling 111 of the first housing 110 and the coupling 121 of the second housing 120 may be configured to be detachably secured to each other such that the at least one input port 112 of the first housing 110 and the at least one input port 122 of the second housing 120 may be positioned on a single side of the connector 100. In other words, the input ports 112 and 122 may be arranged to face outward in a same direction to receive input cables 200 and 300, respectively.

Either the first housing 110 or the second housing 120 may be configured to house, for example, one or more power sources, circuits, processors, memory boards or communications interfaces (not shown) configured to perform one or more functions such as, for example, transmitting data, receiving data, and/or translating protocols across the first and second housings 110, 120.

In some variations, the second housing 120 may provide only an input port without including an output port. Accordingly, the second housing 120 may only be powered and/or communicate when secured or otherwise connected to the first housing 110. As shown in FIG. 1, each of the four pins 301 of the second input cable 300 may be configured to be electrically connected to an internal electrical conduit, and an additional ground point, when the input cable 300 is received by the second input port 122. Accordingly, signals from each of the four pins 301 of the second input cable 300 may be transmitted through the corresponding internal electrical conduit of housing 120, through an electrical conduit provided by the second connection interface 123 coupled between housings 110 and 120, through an internal electrical conduit of housing 110, and, subsequently, output by the output cable 400. Such configuration may minimize the number of the output cables and advantageously improve the flexibility and efficiency of switching from one ECG lead configuration to another without changing the number of the input/output cables.

It should be noted that the numbers and configurations of the pins in each of the first input cable 200 and the second input cable 300 as shown in FIG. 1 is for illustrative purposes only, and it not limited thereto. For example, the numbers of the pins 301 in the second input cable 300 may be four, five or eight with corresponding numbers of internal electrical conduits, depending on different requirements for the monitoring devices. For example, cable 300 and housing 120 shown in FIG. 3 have an increased number of pins and electrical conduits that receive the pins. Thus, inputs and additional housings may have various sizes, widths, or number of electrical paths. Moreover, the pins may be configured in one or more rows, or in different shapes (e.g., circular or oval). Further signal transmission characteristics of the system will be described below with respect to FIGS. 2A, 2B, and 3.

In the embodiment shown in FIGS. 2A and 2B, the couplings 111, 121 may be mechanically interlockable couplings. In other words, the coupling 111 may comprise a female coupling or slot and the coupling 121 may comprise a male coupling or protrusion. Alternatively, or additionally, the coupling 111 may comprise a male coupling or protrusion, and the coupling 121 may comprise a female coupling or slot. In embodiments not shown, the couplings 111, 121 may include one or more magnets. For example, the coupling 111 may include an array of magnets having a first magnetic polarity pattern and the coupling 121 may include an array of magnets having a second magnetic polarity pattern opposite to the first magnetic polarity pattern. As another example, either coupling 111, 121 may be an electro-mechanical coupling.

Either of the first housing 110 or the second housing 120 may include another coupling (not shown) for connecting to another, additional housing (not shown). In other words, additional housing(s) can be added or piggybacked onto the first housing 110 or the second housing 120 to stack three or more housings. In some variations, the additional housing(s) may not include an output port, may only provide an input port, and may only be powered and communicate when secured or otherwise connected to the first housing 110.

In some variations, at least one of the first physiological sensor and the second physiological sensor may be an ECG sensor. Alternatively, or additionally, at least one of the first physiological sensor and the second physiological sensor may be a pulse oximetry sensor. The first housing 110 may be configured to support, for example, six wires from an ECG sensor. Thus, the first housing 110 alone may enable standard ECG monitoring. The second housing 120 may be configured to support, for example, four additional wires from an ECG sensor. Accordingly, the second housing 120 can be quickly secured to the first housing 110 and thereby enable enhanced ECG monitoring. For example, the six leads from input cable 200 and the four leads from input cable 300 may be combined in one output via output port 113 to provide ten leads (electrodes) for a 12-lead configuration. As noted above, in a 12-lead ECG configuration, ten electrodes are placed on predetermined locations of the skin of the patient body. The overall magnitude of the heart's electrical potential is then measured from twelve different angles ("leads") and is recorded over a period of time (e.g., 10 seconds).

In some variations, the at least one output port 113 may be configured to support, for example, ten wires of the output cable 400. Each of the first housing 110 and the second housing 120 may be configured to support any number of wires from a physiological sensor. The at least one output port 113 may be configured to support any number of wires of the output cable 400.

In accordance with various embodiments, the present disclosure may enable the switch from 6-lead ECG configuration to 12-lead ECG configuration in an efficient manner without applying additional cables. This switch between configurations may be seamless, without interruption. As shown in FIG. 1, a first input cable 200 with six pins 201 associated with a first housing 110 may be used alone for 6-lead ECG monitoring, each pin transmitting a physiological signal associated with heart's electrical activity measured on a predetermined location of a patient's body to an output cable 400. By securing a second housing 120 with the first housing 110, the present disclosure may enable the expansion to 12-lead ECG configuration, without applying additional output cables. The additional four pins of the second input cable 300 may be received by the second input port 122, where each of the four pins may transmit physiological signals through corresponding internal electrical conduits to the first housing 110. Likewise, the 12-lead configuration may be switched to the 6-lead configuration easily by detaching the second housing 120 from the first housing 110 without removing cables.

In accordance with various embodiments, the present disclosure may also enable the user to expand or switch the types of the physiological parameters being monitored in an efficient manner without applying additional cables. For example, the first input cable 200 with six pins 201 associated with a first housing 110 may be used alone for 6-lead ECG monitoring. By securing a second housing 120 with the first housing 110, the present disclosure may enable the addition of a SpO2 sensor which monitors the blood saturation level of a patient. Unlike the conventional SpO2 sensor with an independent set of connectors and input and output cables, the embodiments of the present disclosure may advantageously allow various types of physiological parameters to be monitored using one output cable. The two sets of outputs may be output in parallel. Likewise, the SpO2 sensor may easily be removed by detaching the second housing 120 from the first housing 110.

FIG. 2A is a perspective view illustrating the example system including the example implementation of the connector 100, the output cable 400, and the monitor 500. In particular, FIG. 2A is a perspective view of the example system including the example implementation of the connector 100 in which the first housing 110 and the second housing 120 are shown in a detached state.

FIG. 2B is a front view of the first example implementation of the connector 100 including the first housing 110 and the second housing 120. The first housing 110 may include a first connection interface 114 as shown in FIG. 2A and the second housing 120 may include a second connection interface 123 as shown in FIG. 2B. The first connection interface 114 of the first housing 110 may be configured to mate with the second connection interface 123 of the second housing 120 such that the first housing 110 and the second housing 120 may be configured to transmit and/or receive signals to/from each other in a bi-directional manner. For example, the second signal may be transmitted from the second housing 120 to the first housing 110 through the first and second connection interfaces 114 and 123. The first connection interface 114 of the first housing 110 and the second connection interface 123 of the second housing 120 may also enable the transmission of power from the first housing 110 to the second housing 120 or vice versa. In this example, the second connection interface 123 includes a plurality of pins or leads that are configured to be received by or electrically coupled to the first connection interface 114 that includes a plurality of corresponding pin holes, conductive pads, or bonding areas.

In another, non-limiting example of the present disclosure, the signal transmission between the second housing 120 and the first housing 110 may be unidirectional. That is, the second housing 120 may work as an accessary component and be functional for transmitting the second signal to the first housing only when detachably secured to the first housing 110. The second signal may be transmitted from the second housing 120 to the first housing 110, through the second connection interface 123 (shown in FIG. 2B) and the first connection interface 114 (shown in FIG. 2A), respectively. Meanwhile, the first housing 110 may be a host component and function independently by transmitting the first signal to the output cable 400, independent of being detachably secured or unsecured to the second housing 120.

In the embodiment shown in FIGS. 2A and 2B, the first connection interface 114 includes a number of ports (for example, eight) and the first connection interface 114 include a number of pins (for example, eight). Furthermore, any number of pins and/or ports can be used. Alternatively, or additionally, any connection interface enabling signal transmission and/or power transmission can be used.

A signal transmission path of the second signal will be described below with respect to FIGS. 2A and 2B and a signal transmission path of the first signal will be described below with respect to FIG. 3.

In an example implementation, an electrode (not shown) of a second physiological sensor (not shown) may generate a second signal corresponding to a second physiological parameter of a patient. The electrode of the second physiological sensor may be connected to the second input cable 300. The second input cable 300 may include pins 301 which are received in the input port 122 of the second housing 120. The second housing 120 may include the second connection interface 123 configured to mate with the first connection interface 114 of the first housing 110. The first housing 110 may include the output port 113 to which the output cable 400 is connected. The output cable 400 may be further connected to the monitor 500. Accordingly, the second signal may be generated by the electrode of the second physiological sensor, transmitted through the second input cable 300 to the pins 301, transmitted to the input port 122 of the second housing 120, transmitted through internal electrical conduits of the second housing 120 to the second connection interface 123, transmitted through the second connection interface 123 to the first connection interface 114, transmitted through internal electrical conduits of the first housing 110 to input pins (not shown) of the output cable 400, and transmitted through the output cable 400 to the monitor 500.

Figure 3:
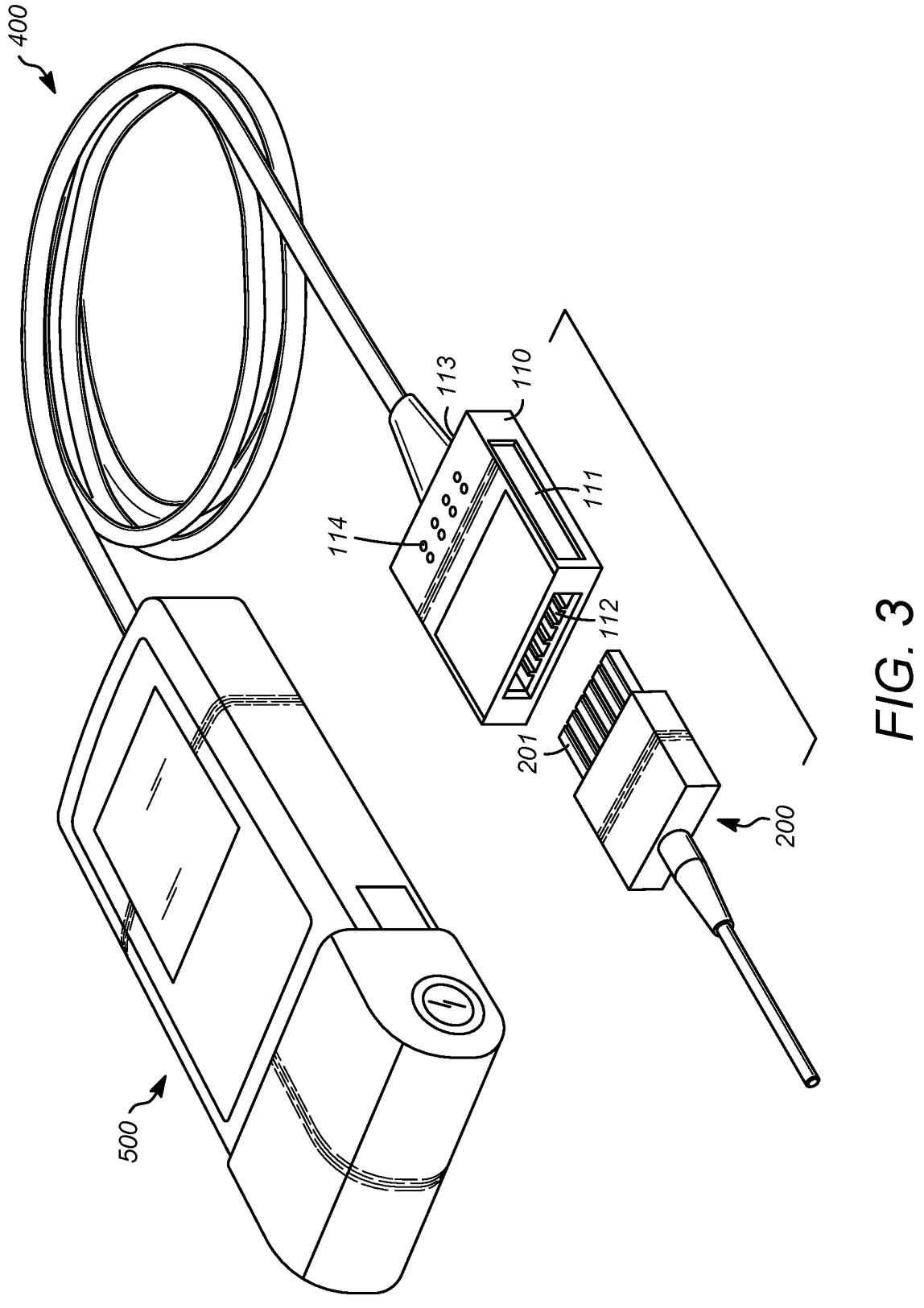
FIG. 3 is a perspective view illustrating the example system including the first housing without the second housing according to one or more embodiments.

FIG. 3 is a perspective view illustrating the example system including the first housing 110, the first input cable 200, the output cable 400, and the monitor 500. In particular, FIG. 3 is a perspective view of the first housing 110 without the second housing 120. As shown in FIG. 3, a first input cable 200 with six pins 201 associated with a first housing 110 may be used alone for 6-lead ECG monitoring, each pin transmitting a physiological signal associated with heart's electrical activity measured on a predetermined location of a patient's body to an output cable 400. In an example implementation, an electrode (not shown) of a first physiological sensor (not shown) may generate a first signal corresponding to a first physiological parameter of a patient. The electrode of the first physiological sensor may be connected to the first input cable 200. The first input cable 200 may include pins 201 which are received in the input port 112 of the first housing 110. The first housing 110 may include the output port 113 to which the output cable 400 is connected. The output cable 400 may be further connected to the monitor 500. Accordingly, the first signal may be generated by the electrode of the first physiological sensor, transmitted through the first input cable 200 to the pins 201, transmitted to the input port 112 of the first housing 110, transmitted through internal electrical conduits of the first housing 110 to the output port 113, transmitted through input pins (not shown) of the output cable 400, and transmitted through the output cable 400 to the monitor 500.

Figure 4:
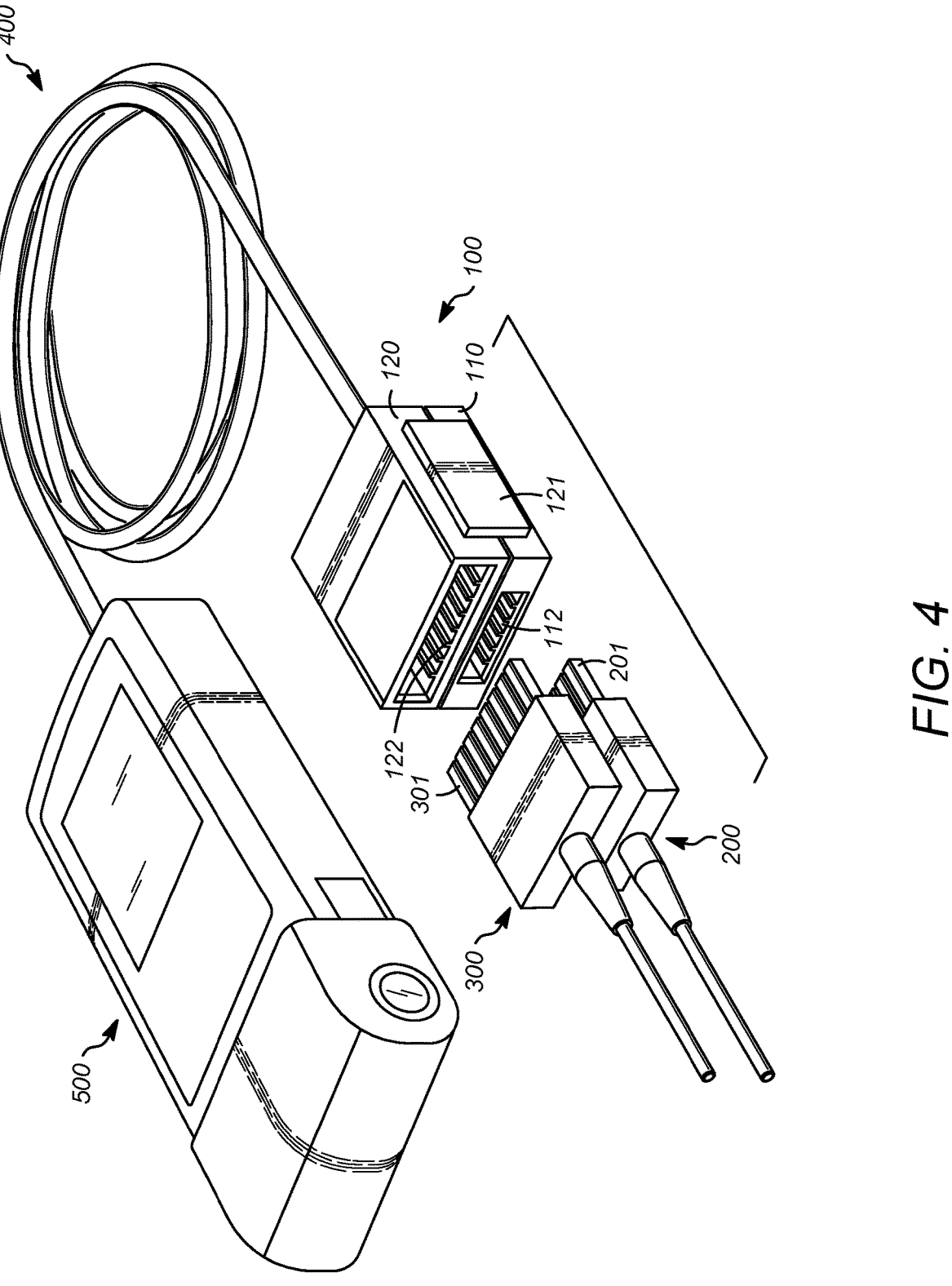
FIG. 4 is an overview of an example system including a second example implementation of a connector according to one or more embodiments.

FIG. 4 is an overview of an example system including a second example implementation of a connector 100. In particular, FIG. 4 is a perspective view illustrating the example system including the second example implementation of the connector 100, a first input cable 200, a second input cable 300, an output cable 400, and a monitor 500. In the embodiment shown in FIG. 4, the connector 100 includes a first housing 110 and a second housing 120. As shown in FIG. 4, a first input cable 200 with six pins 201 associated with a first housing 110 may be used alone for 6-lead ECG monitoring, each pin transmitting a physiological signal associated with heart's electrical activity measured on a predetermined location of a patient's body to an output cable 400. By securing a second housing 120 with the first housing 110, the present disclosure may enable the expansion to 16-lead ECG configuration, without applying additional output cables. The additional eight pins 301 of the second input cable 300 may be received by the second input port 122, where each of the eight pins may transmit physiological signals through corresponding internal electrical conduits to the first housing 110. Each of the eight pins 301 of the second input cable 300 may be configured to be electrically connected to an internal electrical conduit, and an additional ground point, when the input cable 300 is received by the second input port 122. Accordingly, signals from each of the eight pins 301 of the second input cable 300 may transmit through the corresponding internal electrical conduit and subsequently, to the output cable 400.

The first housing 110 may include a first connection interface 114 as shown in FIG. 2A and the second housing 120 may include a second connection interface 123 as shown in FIG. 2B. The first connection interface 114 of the first housing 110 may be configured to mate with the second connection interface 123 of the second housing 120 such that the first housing 110 and the second housing 120 may be configured to be transmit and/or receive signals to/from each other. For example, the second signal may be transmitted from the second housing 120 to the first housing 110 through the first and second connection interfaces 114 and 123. The first connection interface 114 of the first housing 110 and the second connection interface 123 of the second housing 120 may also enable the transmission of power from the first housing 110 to the second housing 120 or vice versa. Likewise, the 16-lead configuration may be switched to the 6-lead configuration easily by detaching the second housing 120 from the first housing 110 without removing cables.

Although FIG. 4 illustrates the eight pins 301 of the second input cable 300 may be configured to be received by the second input port 122 of the second housing 120, in another embodiment of the present disclosure, an additional housing (e.g., a third housing) may be included to expand the ECG lead configuration from 6-lead to 16-lead. The second input port 122 of the second housing 120 may be configured to receive four pins 301 of the second input cable 300 (as shown in e.g., FIG. 1). Additionally, a third housing including a third input port may be configured to be detachably secured with one of the first housing 110 and the second housing 120. The third input port may be configured to receive another four pins of a third input cable. Further, the third housing may comprise connection interfaces (similar to connection interfaces 114 or 123) that enable it to transmit or receive power from the first housing, second housing, or both. The electrical signals received from housings 110, 120, and any additional third housing may be output from the first housing 110 to the output cable 400 simultaneously (in parallel). For example, 6-lead and 4-lead cables may be combined to provide a 12-lead configuration via two housings, 6-lead and 8-lead cables may be combined to provide a 16-lead configuration via two housings (e.g., 14 electrodes are placed on predetermined locations of the skin of the patient body and the overall magnitude of the heart's electrical potential is then measured from sixteen different angles ("leads") and is recorded over a period of time), or 6-lead and two 4-lead cables may be combined to provide a 16-lead configuration via three housings.

As such, the various embodiments of the present disclosure may provide maximal flexibility in accommodating a variety of types and/or numbers of the input cables with numerous lead sets for a clinical provider to use, especially considering the ECG lead sets and/or cables from different manufacturers may have different designs.

As mentioned above, any number of couplings can be located on any surface of the first housing 110 or the second housing 120. Any of the first housing 110 and the second housing 120 may be comprised of plastic. The connector 100 therefore provides flexibility in cable routing by eliminating the need to disconnect a lower capacity connector and replace the lower capacity connector with a higher capacity connector. The connector 100 is modular and scalable and is helpful with respect to seamless workflow in a variety of areas such as monitoring, anesthesia, and information technology workstations. In other words, workflow does not have to be interrupted in order to switch from a lower capacity connection arrangement to a higher capacity connection arrangement. In addition, the connector 100 itself provides a higher capacity connection arrangement itself rather than requiring a device such as a monitor to have a higher capacity connector integrated therein.

Figure 5:
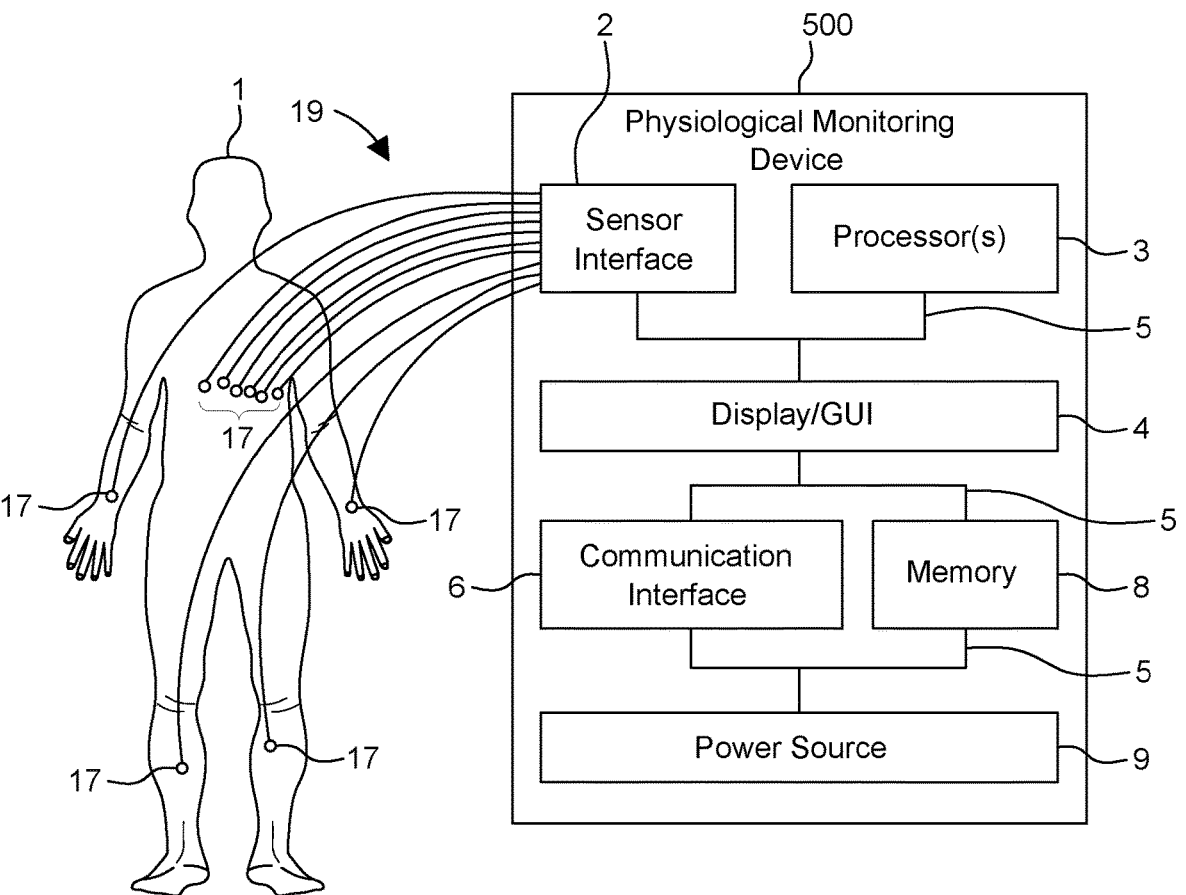
FIG. 5 shows a physiological monitoring system according to one or more embodiments

FIG. 5 shows a physiological monitoring system according to one or more embodiments. As shown in FIG. 5, the system includes a patient monitor 500 (i.e., a physiological monitoring device) capable of receiving physiological data from various sensors 17 connected to a patient 1.

In general, it is contemplated by the present disclosure that the patient monitor 500 includes electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the patient monitor 500 may be adapted to execute any operating system, including Linux, UNIX, Windows Server, etc., as well as virtual machines adapted to virtualize execution of a particular operating system, including customized and proprietary operating systems. The patient monitor 500 is further equipped with components to facilitate communication with other computing devices over one or more network connections, which may include connections to local and wide area networks, wireless and wired networks, public and private networks, and any other communication network enabling communication in the system.

As shown in FIG. 5, the patient monitor 500 is, for example, a patient monitor implemented to monitor various physiological parameters of the patient 1 via the sensors 17. The patient monitor 500 includes a sensor interface 2, one or more processors 3, a display/graphical user interface (GUI) 4, a communication interface 6, a memory 8, and a power source 9. The sensor interface 2 can be implemented in hardware or combination of hardware and software and is used to connect via wired and/or wireless connections 19 to one or more sensors 17 for gathering physiological data from the patient 1. The sensors 17 may be physiological sensors and/or medical devices configured to measure one or more of the physiological parameters and output the measurements via a corresponding one or more connections 19 to the sensor interface 2. Thus, the connections 19 represent one or more wired or wireless communication channels configured to at least transmit sensor data from a corresponding sensor 17 to the sensor interface 2.

By way of example, sensors 17 may include electrodes that attach to the patient for reading electrical signals generated by or passed through the patient 1. Sensors 17 may be configured to measure vital signs, measure electrical stimulation, measure brain electrical activity such as in the case of a electroencephalogram (EEG), measure blood oxygen saturation fraction from absorption of light at different wavelengths as it passes through a finger, measure a carbon dioxide ($CO2$) level and/or other gas levels in an exhalation stream using infrared spectroscopy, measure oxygen saturation on the surface of the brain or other regions, measure cardiac output from invasive blood pressure and temperature measurements, measure induced electrical potentials over the cortex of the brain, measure blood oxygen saturation from an optical sensor coupled by fiber to the tip of a catheter, and/or measure blood characteristics using absorption of light.

The data signals from the sensors 17 include, for example, sensor data related to an electrocardiogram (ECG), non-invasive peripheral oxygen saturation (SpO2), non-invasive blood pressure (NIBP), body temperature, end tidal carbon dioxide (etCO2), apnea detection, and/or other physiological data, including those described herein. The one or more processors 3 are used for controlling the general operations of the patient monitor 500, as well as processing sensor data received by the sensor interface 2. Each one of the one or more processors 3 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the patient monitor 500.

The display/GUI 4 is configured to display various patient data, sensor data, and hospital or patient care information, and includes a user interface implemented for allowing interaction and communication between a user and the patient monitor 500. The display/GUI 4 includes, but is not limited to, a keyboard, a liquid crystal display (LCD), cathode ray tube (CRT) display, thin film transistor (TFT) display, light-emitting diode (LED) display, high definition (HD) display, or other similar display device that may include touch screen capabilities. The display/GUI 4 also provides a means for inputting instructions or information directly to the patient monitor 500. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators).

The communication interface 6 enables the patient monitor 500 to directly or indirectly (via, for example, a monitor mount) communicate with one or more computing networks and devices, including one or more sensors 17, workstations, consoles, computers, monitoring equipment, alert systems, and/or mobile devices (e.g., a mobile phone, tablet, or other hand-held display device). The communication interface 6 can include various network cards, interfaces, communication channels, cloud, antennas, and/or circuitry to enable wired and wireless communications with such computing networks and devices. The communication interface 6 can be used to implement, for example, a Bluetooth connection, a cellular network connection, and/or a Wi-Fi connection with such computing networks and devices. Example wireless communication connections implemented using the communication interface 6 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol). In essence, any wireless communication protocol may be used.

Additionally, the communication interface 6 can enable direct (i.e., device-to-device) communications (e.g., messaging, signal exchange, etc.) such as from a monitor mount to the patient monitor 500 using, for example, a universal serial bus (USB) connection or other communication protocol interface. The communication interface 6 can also enable direct device-to-device connection to other device such as to a tablet, computer, or similar electronic device; or to an external storage device or memory.

The memory 8 can be a single memory device or one or more memory devices at one or more memory locations that include, but is not limited to, a random access memory (RAM), a memory buffer, a hard drive, a database, an erasable programmable read only memory (EPROM), an electrically erasable programmable read only memory (EEPROM), a read only memory (ROM), a flash memory, hard disk, various layers of memory hierarchy, or any other non-transitory computer readable medium. The memory 8 can be used to store any type of instructions and patient data associated with algorithms, processes, or operations for controlling the general functions and operations of the patient monitor 500.

The power source 9 can include a self-contained power source such as a battery pack and/or include an interface to be powered through an electrical outlet (either directly or by way of a monitor mount). The power source 9 can also be a rechargeable battery that can be detached allowing for replacement. In the case of a rechargeable battery, a small built-in back-up battery (or super capacitor) can be provided for continuous power to be provided to the patient monitor 500 during battery replacement. Communication between the components of the patient monitor 500 (e.g., components 2, 3, 4, 6, 8, and 9) are established using an internal bus 5.

Accordingly, the patient monitor 500 is attached to one or more of several different types of sensors 17 configured to measure and readout physiological data related to the patient 1 (e.g., as shown on the left side of FIG. 5). One or more sensors 17 may be attached to patient monitor 500 by, for example, a wired connection coupled to the sensor interface 2. Additionally, or alternatively, one or more sensors 17 may be a wireless sensor that is communicatively coupled to the patient monitor 500 via the communication interface 6, which includes circuity for receiving data from and sending data to one or more devices using, for example, a Wi-Fi connection, a cellular network connection, and/or a Bluetooth connection.

The data signals from the sensors 17 received by the patient monitor 500 may include sensor data related to, for example, body temperature (BT), pulse (heart rate (HR)), and breathing rate (respiratory rate) (RR), an ECG, SpO2, NIBP, and/or etCO2.

The data signals received from the sensors, including an ECG sensor and an SpO2 sensor, can be analog signals. For example, the data signals for the ECG and the SpO2 are input to the sensor interface 2, which can include an ECG data acquisition circuit and an SpO2 data acquisition circuit. Both the ECG data acquisition circuit and the SpO2 data acquisition circuit may include amplifying and filtering circuity as well as analog-to-digital (A/D) circuity that converts the analog signal to a digital signal using amplification, filtering, and A/D conversion methods. In the event that the ECG sensor and the SpO2 sensor are wireless sensors, the sensor interface 2 may receive the data signals from a wireless commination module. Thus, a sensor interface is a component configured to interface with one or more sensors 17 and receive sensor data therefrom.

As another example, the data signals related to NIBP, body temperature, and etCO2 can be received from sensors 17 to the sensor interface 2, which can include a physiological parameter interface such as serial interface circuitry for receiving and processing the data signals related to NIBP, temperature, and etCO2. In FIG. 5, the ECG data acquisition circuit, an SpO2 data acquisition circuit, and physiological parameter interface are described as part of the sensor interface 2. However, it is contemplated by the present disclosure that the ECG data acquisition circuit, the SpO2 data acquisition circuit, and physiological parameter interface can be implemented as circuits separate from the sensor interface 2. In the event that the NIBP sensor, the temperature sensor, and the etCO2 sensor are wireless sensors, the sensor interface 2 may receive the data signals from a wireless commination module.

The processing performed by the ECG data acquisition circuit, the SpO2 data acquisition circuit, and external physiological parameter interface may generate analog data waveforms or digital data waveforms that are analyzed by a microcontroller. The microcontroller may be one of the processors 3. The microcontroller, for example, analyzes the digital waveforms to identify certain digital waveform characteristics and threshold levels indicative of conditions (abnormal and normal) of the patient 1 using one or more monitoring methods. A monitoring method may include comparing an analog or a digital waveform characteristic or an analog or digital value to one or more threshold values and generating a comparison result based thereon. The microcontroller is, for example, a processor, an FPGA, an ASIC, a DSP, a microcontroller, or similar processing device. The microcontroller includes a memory or uses a separate memory 8. The memory is, for example, a RAM, a memory buffer, a hard drive, a database, an EPROM, an EEPROM, a ROM, a flash memory, a hard disk, or any other non-transitory computer readable medium.

The memory stores software or algorithms with executable instructions and the microcontroller can execute a set of instructions of the software or algorithms in association with executing different operations and functions of the patient monitor 500 such as analyzing the digital data waveforms related to the data signals from the sensors 17.

Although various embodiments have been described above, these are to be regarded as merely examples. Accordingly, those of ordinary skill in the art will recognize that various changes and modifications of the examples described herein can be made without departing from the spirit and scope of the present disclosure. For example, any feature of any particular portion, embodiment or modification of the system may be included or omitted from any of the other portions, embodiments or modifications of the system.

It is also contemplated that the implementation of the components of the present disclosure can be done with any newly arising technology that may replace any of the above implementation technologies.

The system of the present disclosure provides an integrated, modular and scalable connector capable of quickly and/or compactly expanding the number of input ports for cables, and therefore the number of devices, that can be supported.

What is claimed is:

1. A modular connector, comprising:
   a first housing comprising a first input port, a first connection interface, and an output port, wherein the first housing is configured to detachably secure a first input cable of a first physiological sensor at the first input port so as to be configured to receive at least one first signal via the first input cable upon connection of the first input cable to the first input port;
   a second housing comprising a second input port and a second connection interface, wherein the second housing is configured to detachably secure a second input cable of a second physiological sensor at the second input port so as to be configured to receive at least one second signal via the second input cable upon connection of the second input cable to the second input port, the second connection interface being configured to electrically couple with the first connection interface to transmit the at least one second signal, via the second input cable connected to the second input port, to the first housing; and
   a coupling mechanism configured to detachably secure the second housing to the first housing such that the second connection interface and the first connection interface are in electrical contact,
   wherein the first housing is configured to simultaneously route the at least one first signal from the first input port via the first input cable connected to the first input port, and to route the at least one second signal from the first connection interface via the second input cable connected to the second input port to the output port.

2. The modular connector of claim 1, wherein the at least one first signal configured to be received by the first input port upon the first input cable being connected thereto and the at least one second signal configured to be received by the second input port upon the second input cable being connected thereto are electrocardiogram (ECG) signals.

3. The modular connector of claim 2, wherein the at least one first signal is configured for a first ECG lead configuration, the at least one second signal is configured for a second ECG lead configuration, and the first housing is configured to simultaneously output the at least one first signal and the at least one second signal from the output port for a third ECG lead configuration that is different from the first ECG lead configuration and the second ECG lead configuration.

4. The modular connector of claim 1, wherein the at least one first signal configured to be received by the first input port upon the first input cable being connected thereto and the at least one second signal configured to be received by the second input port upon the second input cable being connected thereto are a combination of electrocardiogram (ECG) signals and pulse oximetry signals.

5. The modular connector of claim 1, wherein the at least one first signal configured to be received by the first input port upon the first input cable being connected thereto represents a first type of physiological parameter and the at least one second signal configured to be received by the second input port upon the second input cable being connected thereto represents a second type of physiological parameter that is different from the first type of physiological parameter.

6. The modular connector of claim 1, wherein the first housing comprises a first portion of the coupling mechanism and the second housing comprises a second portion of the coupling mechanism.

7. The modular connector of claim 1, wherein:
the first connection interface and the second connection interface are bidirectional connection interfaces, and
the first connection interface is configured to transmit a power signal from the first housing to the second housing via the second connection interface.

8. The modular connector of claim 1, wherein the first housing is configured to simultaneously receive the at least one first signal and the at least one second signal.

9. A modular connector system, comprising:
a first connector comprising a first input port, a first connection interface, and an output port, wherein the first connector is configured to detachably secure a first input cable of a first physiological sensor at the first input port so as to be configured to receive at least one first signal via the first input cable upon connection of the first input cable to the first input port;
a second connector comprising a second input port and a second connection interface, wherein the second connector is configured to detachably secure a second input cable of a second physiological sensor at the second input port so as to be configured to receive at least one second signal via the second input cable upon connection of the second input cable to the second input port, the second connection interface being configured to electrically couple with the first connection interface to transmit the at least one second signal via the second input cable connected to the second input port to the first connector; and a coupling mechanism configured to detachably secure the second connector to the first connector such that the second connection interface and the first connection interface are in electrical contact,
wherein the first connector is configured to simultaneously route the at least one first signal from the first input port via the first input cable connected to the first input port, and to route the at least one second signal from the first connection interface, via the second input cable connected to the second input port, to the output port.

10. A system, comprising:
a monitoring device configured to receive and process a plurality of physiological sensor signals;
a connector comprising:
a first housing comprising a first input port, a first connection interface, and an output port, wherein the first housing is configured to detachably secure a first input cable of a first physiological sensor at the first input port so as to be configured to receive at least one first signal via the first input cable, upon connection of the first input cable to the first input port;
a second housing comprising a second input port and a second connection interface, wherein the second housing is configured to detachably secure a second input cable of a second physiological sensor at the second input port so as to be configured to receive at least one second signal via the second input cable upon connection of the second input cable to the second input port, the second connection interface being configured to electrically couple with the first connection interface to transmit the at least one second signal, via the second input cable connected to the third connection interface, to the first housing; and
a coupling mechanism configured to detachably secure the second housing to the first housing such that the second connection interface and the second connection interface are in electrical contact,
wherein the first housing houses is configured to simultaneously route the at least one first signal from the first connection interface via the first input cable connected to the first connection interface, and to route the at least one second signal from the second connection interface via the second input cable connected to the third connection interface to the output port; and
an output cable configured to be detachably secured to and between the output port of the first housing and to the monitoring device such that the monitoring device, upon being connected via its output cable to the output port of the first housing, receives selectively routed signals from the first housing.

11. The system of claim 10, wherein:
the first input cable configured to be received by the first input port upon connection thereto is a first electrocardiogram (ECG) cable comprising a first number of ECG leads,
the second input cable configured to be received by the second input port upon connection thereto is a second ECG cable comprising a second number of ECG leads, and
the monitoring device upon its output cable being secured to the output port of the first housing is configured to automatically detect the first number of ECG leads and the second number of ECG leads, and automatically determine an ECG lead configuration that optimizes a total number of ECG leads, and automatically adjust configuration settings according to the determined ECG lead configuration.

12. The system of claim 11, wherein:

in response to a disconnect of the second input cable from the second housing, the monitoring device is configured to automatically determine the ECG lead configuration that optimizes the total number of ECG leads being reduced by the disconnect of the second input cable from the second housing, and automatically adjust the configuration settings according to the determined ECG lead configuration.

13. The system of claim 10, wherein:

the first input cable configured to be received by the first input port upon connection thereto is an electrocardiogram (ECG) cable, the second input cable configured to be received by the second input port upon connection thereto is a pulse oximetry cable, and the monitoring device upon its output cable being secured to the output port of the first housing is configured to automatically detect data types of the first input cable and the second input cable for the processing thereof.

14. The modular connector of claim 1, wherein:

the first input port and the first connection interface are located at first and second sides of the first housing, respectively, the first and the second sides being perpendicular to each other, and the second input port and second connection interface are located at third and fourth sides of the second housing, respectively, the third and the fourth sides being perpendicular to each other, wherein the second and the fourth sides are configured to be in direct contact with each other when the first housing is coupled to the second housing such that the first connection interface is in direct electrical contact with the second connection interface.

15. The modular connector of claim 14, wherein:

the first input port is configured to be directly coupled to the first input cable for directly receiving the at least one first signal therefrom, the second input port is configured to be directly coupled to the second input cable for directly receiving the at least one second signal therefrom, when the first housing is coupled to the second housing, the first connection interface is in direct electrical contact with the second connection interface, and when the first housing is coupled to the second housing, the at least one second signal is routed from the second input cable, through the second housing, though the first and the second connection interfaces, through the first housing, to the output port, and the at least one first signal is routed from the first input cable, through the first housing, to the output port such that the output port simultaneously receives and outputs the at least one first signal and the at least one second signal.

16. The modular connector of claim 14, wherein the first input port is configured to be directly coupled to the first input cable for directly receiving the at least one first signal therefrom, the second input port is configured to be directly coupled to the second input cable for directly receiving the at least one second signal therefrom, when the first housing is coupled to the second housing, the first connection interface is in direct electrical contact with the second connection interface, and when the first housing is coupled to the second housing, the at least one second signal is routed from the second input cable, through the second housing, though the first and the second connection interfaces, to the first housing and combined with the at least one first signal from the first housing into an output signal that is configured to be output by the output port.

17. The modular connector of claim 16, wherein the at least one first signal is configured for a first electrocardiogram (ECG) lead configuration, the at least one second signal is configured for a second ECG lead configuration, and the first housing is configured to combine the at least one first signal and the at least one second signal to generate the output signal configured for a third ECG lead configuration that is different from the first ECG lead configuration and the second ECG lead configuration.

18. The system of claim 10, wherein:

the at least one first signal includes at least one first sensor signal corresponding to a first type of physiological parameter and a first configuration signal indicating a cable type of the first input cable, the at least one second signal includes at least one second sensor signal corresponding to a second type of physiological parameter and a second configuration signal indicating a cable type of the second input cable, wherein the monitoring device is configured to receive the first configuration signal and the second configuration signal from the output cable, automatically determine a monitor configuration based on the first configuration signal and the second configuration signal, and process the at least one first signal and the at least one second signal based on the determined monitor configuration.

19. The system of claim 18, wherein the first configuration signal includes first EEPROM data and the second configuration signal includes second EEPROM data.

20. The system of claim 11, wherein:

the at least one first signal includes at least one first sensor signal corresponding to a first type of physiological parameter and a first configuration signal indicating the first number of ECG leads of the first input cable, the at least one second signal includes at least one second sensor signal corresponding to a second type of physiological parameter and a second configuration signal indicating the second number of ECG leads of the second input cable, and wherein the monitoring device is configured to receive the first configuration signal and the second configuration signal from the output cable, automatically determine the total number of ECG leads as the sum of the first number of ECG leads and the second number of ECG leads, automatically determine the ECG lead configuration that optimizes the total number of ECG leads, wherein the ECG lead configuration changes as the total number of ECG leads changes, and automatically adjust configuration settings of the monitoring device according to the determined ECG lead configuration.

21. The system of claim 20, wherein the monitoring device is configured to simultaneously process the at least one first signal and the at least one second signal based on the configuration settings of the monitoring device.

* * * * *